United States Patent
Curbera et al.

(10) Patent No.: US 11,355,231 B2
(45) Date of Patent: *Jun. 7, 2022

(54) SCALABLE AND TRACEABLE HEALTHCARE ANALYTICS MANAGEMENT

(71) Applicant: International Business Machines Corporation, Armonk, NY (US)

(72) Inventors: Francisco P. Curbera, Hastings on Hudson, NY (US); Shilpa N. Mahatma, Mohegan Lake, NY (US); Yajuan Wang, White Plains, NY (US); Rose M. Williams, Wappinger Falls, NY (US); Gigi Y. C. Yuen-Reed, Tampa, FL (US)

(73) Assignee: International Business Machines Corporation, Armonk, NY (US)

( * ) Notice: Subject to any disclaimer, the term of this patent is extended or adjusted under 35 U.S.C. 154(b) by 690 days.

This patent is subject to a terminal disclaimer.

(21) Appl. No.: 15/833,044

(22) Filed: Dec. 6, 2017

(65) Prior Publication Data

US 2018/0276343 A1 Sep. 27, 2018

Related U.S. Application Data

(63) Continuation of application No. 15/467,211, filed on Mar. 23, 2017.

(51) Int. Cl.
*G16H 40/20* (2018.01)
*G16H 50/70* (2018.01)
*G16H 70/20* (2018.01)

(52) U.S. Cl.
CPC ............ *G16H 40/20* (2018.01); *G16H 50/70* (2018.01); *G16H 70/20* (2018.01)

(58) Field of Classification Search
None
See application file for complete search history.

(56) References Cited

U.S. PATENT DOCUMENTS 7,191,183 B1 3/2007 Goldstein
8,200,527 B1 * 6/2012 Thompson
(Continued)

FOREIGN PATENT DOCUMENTS

CN 104541268 A 4/2015
JP 2011517993 A 6/2011
(Continued)

OTHER PUBLICATIONS

"SAS Model Manager: Create, manage, monitor and govern analytical models", SAS, Fact Sheet, (month unknown) 2015, 4 pages. [as cited by Applicant in parent application Information Disclosure Statement filed on Mar. 23, 2017; U.S. Appl. No. 15/467,211] (Year: 2015).*

(Continued)

*Primary Examiner* — Lynda Jasmin
*Assistant Examiner* — Shaun D Sensenig
(74) *Attorney, Agent, or Firm* — Stephen R. Tkacs; Stephen J. Walder, Jr.; Aaron Pontikos

(57) ABSTRACT

A mechanism is provided to implement a healthcare analytics management system. A healthcare analytics development sub-system develops an analytics pipeline of a set of analytics assets for a selected healthcare based on a set of business needs for a healthcare analytics client and a healthcare analytics model based on the set of analytics assets and the set of business needs. A model deployment module of a healthcare analytics operation sub-system deploys the healthcare analytics model on a set of computing devices of the selected healthcare consumer. Responsive to detecting a performance deviation of the deployed healthcare analytics (Continued)

model from the set of business needs, a model feedback module determines improvement needs for the healthcare analytics model. The model feedback module feeds the improvement needs back to the healthcare analytics development sub-system. The healthcare analytics development sub-system customizes the healthcare analytics model based on the improvement needs.

16 Claims, 6 Drawing Sheets

(56) References Cited

U.S. PATENT DOCUMENTS

| | | | |
|---|---|---|---|
| 8,370,280 B1* | 2/2013 | Lin | G06N 20/00 706/12 |
| 9,542,566 B2* | 1/2017 | Yu | G06F 8/71 |
| 2006/0007471 A1 | 4/2006 | Funk et al. | |
| 2009/0287678 A1 | 11/2009 | Brown et al. | |
| 2011/0066587 A1 | 3/2011 | Ferrucci et al. | |
| 2011/0125734 A1 | 5/2011 | Duboue et al. | |
| 2012/0191475 A1 | 7/2012 | Pandey | |
| 2013/0007055 A1 | 1/2013 | Brown et al. | |
| 2013/0018652 A1 | 1/2013 | Ferrucci et al. | |
| 2013/0066886 A1 | 3/2013 | Bagchi et al. | |
| 2013/0191157 A1 | 7/2013 | Elden et al. | |
| 2013/0246996 A1* | 9/2013 | Duggal | |
| 2013/0253942 A1 | 9/2013 | Liu et al. | |
| 2015/0025925 A1* | 1/2015 | Moore | |
| 2015/0100331 A1 | 4/2015 | Roychowdhury | |
| 2015/0149235 A1 | 5/2015 | Leung | |
| 2015/0213458 A1 | 7/2015 | Wolniewicz | |
| 2016/0019357 A1* | 1/2016 | Marzula | |
| 2016/0071171 A1* | 3/2016 | Cancelliere, III | |
| 2016/0232312 A1 | 8/2016 | Apte et al. | |

FOREIGN PATENT DOCUMENTS

| | | |
|---|---|---|
| JP | 2015103212 A | 6/2015 |
| JP | 2015529881 A | 10/2015 |
| WO | WO2016/168359 A1 | 10/2016 |

OTHER PUBLICATIONS

"Better business outcomes with IBM Big Data & Analytics", IBM Corporation, IBM Software Group Whitepaper, Jan. 21, 2014, 12 pages.
"Beyond the EHR: IT Transformation for a Digital World", OPTUM, TechTarget Custom Media, White Paper, (month known) 2016, 5 pages.
"IBM SPSS Modeler", IBM Corporation, IBM Analytics, SPSS Software, Feb. 2016, 8 pages.
"SAS Model Manager: Create, manage, monitor and govern analytical models", SAS, Fact Sheet, (month unknown) 2015, 4 pages.
"SPSS Collaboration and Deployment Services", IBM Corporation, IBM Software Products Advanced analytics Prescriptive analytics, Jul. 7, 2016, 2 pages.
Biem, Alain et al., "Towards Cognitive Automation of Data Science", Association for the Advancement of Artificial Intelligence, (month unknown) 2015, 2 pages.
High, Rob, "The Era of Cognitive Systems: An Inside Look at IBM Watson and How it Works", IBM Corporation, Redbooks, Dec. 12, 2012, 16 pages.
McCord, M.C et al., "Deep parsing in Watson", IBM J. Res. & Dev. vol. 56 No. 3/4 Paper 3, May/Jul. 2012, pp. 3:1-3:15.
Ng, Kenney et al., "PARAMO: A Parallel Predictive Modeling Platform for Healthcare Analytic Research using Electronic Health Records", National Institutes of Health, NIH Public Access, Author Manuscript, Apr. 2014, 29 pages.
Ronanki, Rajeev et al., "Industrialized analytics", Deloitte university Press, Tech Trends 2016: Innovating in the digital era, (month unknown) 2016, pp. 96-111.
Yuan, Michael J. , "Watson and Healthcare, How natural language processing and semantic search could revolutionize clinical decision support", IBM Corporation, developerWorks, http://www.ibm.com/developerworks/industry/library/ind-watson/, Apr. 12, 2011, pp. 1-14.
List of IBM Patents or Patent Applications Treated as Related, Dec. 6, 2017, 2 pages,.
International Search Report and Written Opinion dated Jul. 18, 2018 for International Application No. PCT/IB2018/051933, 10 pages.

* cited by examiner

SCALABLE AND TRACEABLE HEALTHCARE ANALYTICS MANAGEMENT

BACKGROUND

The present application relates generally to an improved data processing apparatus and method and more specifically to mechanisms for scalable and traceable healthcare analytics management.

Healthcare analytics is a term used to describe analysis activities that can be undertaken as a result of data collected from four areas within healthcare: claims and cost data, pharmaceutical and research and development data, clinical data collected from electronic medical records (EMRs), and patient behavior and sentiment data (e.g., patient behaviors and preferences and retail purchases). Healthcare analytics focuses on areas of clinical analysis, financial analysis, supply chain analysis, fraud, and human resources analysis. Healthcare analytics allows for the examination of patterns in various healthcare data in order to determine how clinical care can be improved while limiting excessive spending.

SUMMARY

This Summary is provided to introduce a selection of concepts in a simplified form that are further described herein in the Detailed Description. This Summary is not intended to identify key factors or essential features of the claimed subject matter, nor is it intended to be used to limit the scope of the claimed subject matter.

In one illustrative embodiment, a method is provided in a data processing system comprising at least one processor and at least one memory, the at least one memory comprising instructions executed by the at least one processor to cause the at least one processor to implement a healthcare analytics management system. The method comprises developing, by a healthcare analytics development sub-system of the healthcare analytics management system, an analytics pipeline of a set of analytics assets for a selected healthcare based on a set of business needs for a healthcare analytics client and a healthcare analytics model based on the set of analytics assets and the set of business needs. The healthcare analytics model links to the analytics pipeline. The method further comprises deploying, by a model deployment module of a healthcare analytics operation sub-system of the healthcare analytics management system, the healthcare analytics model on a set of computing devices of the selected healthcare consumer. The method further comprises, responsive to a model monitoring module of the healthcare analytics operation sub-system detecting a performance deviation of the deployed healthcare analytics model for performance deviation from the set of business needs for the healthcare analytics client, determining, by a model feedback module of the healthcare analytics operation sub-system, improvement needs for the healthcare analytics model. The method further comprises feeding, by the model feedback module, the improvement needs back to the healthcare analytics development sub-system. The method further comprises customizing, by the healthcare analytics development sub-system, the healthcare analytics model based on the improvement needs.

In other illustrative embodiments, a computer program product comprising a computer useable or readable medium having a computer readable program is provided. The computer readable program, when executed on a computing device, causes the computing device to perform various ones of, and combinations of, the operations outlined above with regard to the method illustrative embodiment.

In yet another illustrative embodiment, a system/apparatus is provided. The system/apparatus may comprise one or more processors and a memory coupled to the one or more processors. The memory may comprise instructions which, when executed by the one or more processors, cause the one or more processors to perform various ones of, and combinations of, the operations outlined above with regard to the method illustrative embodiment.

These and other features and advantages of the present invention will be described in, or will become apparent to those of ordinary skill in the art in view of, the following detailed description of the example embodiments of the present invention.

BRIEF DESCRIPTION OF THE DRAWINGS

The invention, as well as a preferred mode of use and further objectives and advantages thereof, will best be understood by reference to the following detailed description of illustrative embodiments when read in conjunction with the accompanying drawings, wherein.

DETAILED DESCRIPTION

Figure 1:
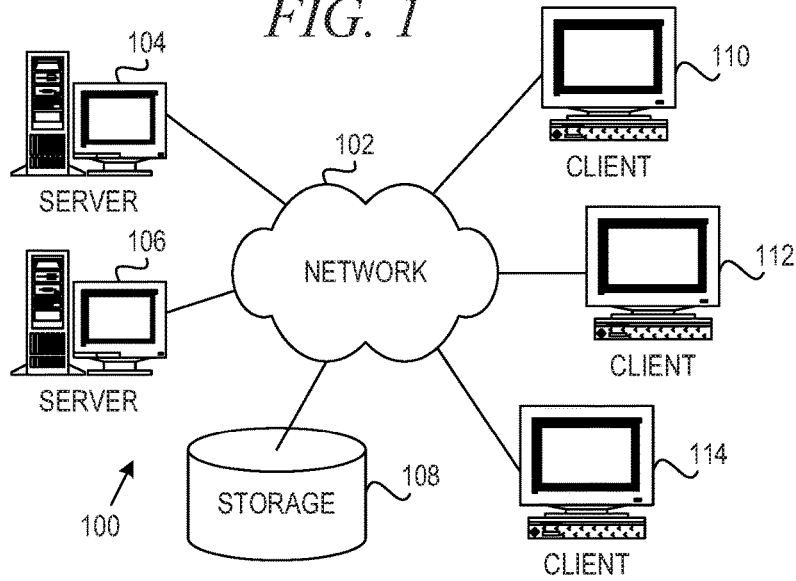
FIG. 1 is an example diagram of a distributed data processing system in which aspects of the illustrative embodiments may be implemented.

There is a rising need fir identifying and applying data-driven evidence to improve care outcome and lower cost. Identification of data-driven evidence requires highly skilled resources using advanced analytics methods (e.g., machine learning or pattern detection). For a healthcare practitioner, a patient, or a policy maker to benefit from the data-driven evidence, the analytics assets must be deployed as near real-time applications and integrated with operational systems. Each patient population has unique and varying healthcare needs, leading to different analytics requirements. Dynamic market environment and medical practice demand the ability to flexibly adapt analytics models over time.

However, health evidence data tends to be scattered across organizations and data systems. Deriving evidence-based insights tends to be a manual and ad hoc process, lacking standard end-to-end workflow. In the prior art, there is no organized way to reuse, share, and manage analytics assets and no traceable way to deploy analytics assets. The prior art solutions lack a feedback loop to adapt analytics based on new evidence or new data sources.

The illustrative embodiments provide mechanisms for cloud-based traceable and scalable healthcare analytics management. The mechanisms of the illustrative embodiments orchestrate development, deployment, and operation in a closed loop to enable analytics life cycle governance and continuous learning. The mechanisms of the illustrative embodiments provide insights as a service for a variety of different healthcare consumers. The illustrative embodiments address the critical challenges in management of a large number of a variety of different healthcare analytics assets, including traceability, reusability, search-ability, extensibility, automated application, and continuous improvement.

The mechanisms of the illustrative embodiments include the following two sub-systems: a management system of healthcare analytics development and a management system of healthcare analytics operation. The management system of healthcare analytics development is composed of versioned analytics repositories with libraries of functions in each step of analytics workflow for different business purposes and versioned model repositories linked with analytics repositories as well as extended application programming interface (API) services. The management system of healthcare analytics operation includes the following modules: a model deployment module plugging the right version of model developed in the right workflow/runtime environment and actively managing the associated metadata; a model monitoring module periodically reporting the performance of deployed models and detecting and notifying of a performance deviation; and, a model feedback mechanism analyzing the potential root causes of performance deviation, reasoning improvement needs, and feeding back improvement requirements to analytics development management.

The illustrative embodiments provide mechanisms for cloud-based healthcare analytics life-cycle management, including development and operation, especially for multiple-client model customization, deployment, and operation feedback. The illustrative embodiments separate the analytics repository from the model repository. The analytics repository provides an analytics pipeline designed for each clinical or business use case, such as a pipeline for readmission risks using electronic medical records (EMRs). The model repository provides a tuned analytics model given specific data inputs and configurations, such as a readmission risk model developed for the Medicare population served by a particular health system.

In accordance with an illustrative embodiment, each repository has reusable libraries with functions and standard workflow designed for its intended purposes. A library builder adds annotations or tags to indicate metadata about the library to make it searchable. Application programming interface (API) services make the reusability and shareability easier and also enable the collaboration.

The illustrative embodiments support configurable analytics assets. Configurations are exposed through API services to minimize manual code changes. Each configuration includes analytics parameters specific to a use case, metadata specific to the data set. Configurations make the deployed model traceable.

The illustrative embodiments provide multi-level versioning of deployed analytics assets. For example, level 1 is the training pipeline, level 2 is the customized model for a client, and level 3 is enhancement over time based on the client's data feedback. The mechanisms of the illustrative embodiments can revert back to an old configuration and can make past configurations searchable.

The illustrative embodiments provide closed-loop model monitoring, adaptive customization, and continuous learning feedback mechanism. The monitoring function establishes the runtime performance and detects the performance deviation. The feedback mechanism reasons the performance deviation as well as different level improvement needs (e.g., low touch parameter retuning vs. high touch model retraining from analytics pipeline, etc.). The model updating mechanism provides feedback to the development analytics pipeline and model repository to enable continuous learning.

Before beginning the discussion of the various aspects of the illustrative embodiments, it should first be appreciated that throughout this description the term "mechanism" will be used to refer to elements of the present invention that perform various operations, functions, and the like. A "mechanism," as the term is used herein, may be an implementation of the functions or aspects of the illustrative embodiments in the form of an apparatus, a procedure, or a computer program product. In the case of a procedure, the procedure is implemented by one or more devices, apparatus, computers, data processing systems, or the like. In the case of a computer program product, the logic represented by computer code or instructions embodied in or on the computer program product is executed by one or more hardware devices in order to implement the functionality or perform the operations associated with the specific "mechanism." Thus, the mechanisms described herein may be implemented as specialized hardware, software executing on general purpose hardware, software instructions stored on a medium such that the instructions are readily executable by specialized or general purpose hardware, a procedure or method for executing the functions, or a combination of any of the above.

The present description and claims may make use of the terms "a," "at least one of," and "one or more of" with regard to particular features and elements of the illustrative embodiments. It should be appreciated that these terms and phrases are intended to state that there is at least one of the particular feature or element present in the particular illustrative embodiment, but that more than one can also be present. That is, these terms/phrases are not intended to limit the description or claims to a single feature/element being present or require that a plurality of such features/elements be present. To the contrary, these terms/phrases only require at least a single feature/element with the possibility of a plurality of such features/elements being within the scope of the description and claims.

Moreover, it should be appreciated that the use of the term "engine," if used herein with regard to describing embodiments and features of the invention, is not intended to be limiting of any particular implementation for accomplishing and/or performing the actions, steps, processes, etc., attributable to and/or performed by the engine. An engine may be, but is not limited to, software, hardware and/or firmware or any combination thereof that performs the specified functions including, but not limited to, any use of a general and/or specialized processor in combination with appropriate software loaded or stored in a machine readable memory and executed by the processor. Further, any name associated with a particular engine is, unless otherwise specified, for purposes of convenience of reference and not intended to be limiting to a specific implementation. Additionally, any functionality attributed to an engine may be equally performed by multiple engines, incorporated into and/or combined with the functionality of another engine of the same or different type, or distributed across one or more engines of various configurations.

In addition, it should be appreciated that the following description uses a plurality of various examples for various elements of the illustrative embodiments to further illustrate example implementations of the illustrative embodiments and to aid in the understanding of the mechanisms of the illustrative embodiments. These examples intended to be non-limiting and are not exhaustive of the various possibilities for implementing the mechanisms of the illustrative embodiments. It will be apparent to those of ordinary skill in the art in view of the present description that there are many other alternative implementations for these various elements that may be utilized in addition to, or in replacement of, the examples provided herein without departing from the spirit and scope of the present invention.

Figure 2:
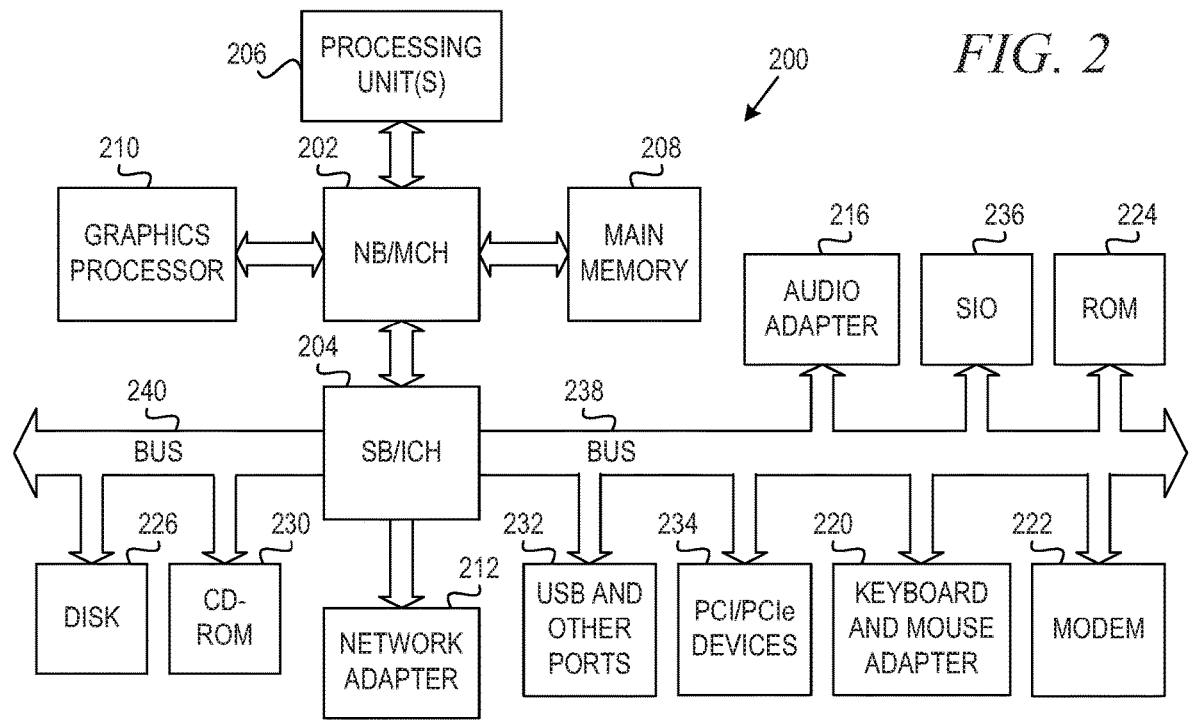
FIG. 2 is an example block diagram of a computing device in which aspects of the illustrative embodiments may be implemented.

The illustrative embodiments may be utilized in many different types of data processing environments. In order to provide a context for the description of the specific elements and functionality of the illustrative embodiments, FIGS. 1 and 2 are provided hereafter as example environments in which aspects of the illustrative embodiments may be implemented. It should be appreciated that FIGS. 1 and 2 are only examples and are not intended to assert or imply any limitation with regard to the environments in which aspects or embodiments of the present invention may be implemented. Many modifications to the depicted environments may be made without departing from the spirit and scope of the present invention.

FIG. 1 depicts a pictorial representation of an example distributed data processing system in which aspects of the illustrative embodiments may be implemented. Distributed data processing system 100 may include a network of computers in which aspects of the illustrative embodiments may be implemented. The distributed data processing system 100 contains at least one network 102, which is the medium used to provide communication links between various devices and computers connected together within distributed data processing system 100. The network 102 may include connections, such as wire, wireless communication links, or fiber optic cables.

In the depicted example, server 104 and server 106 are connected to network 102 along with storage unit 108. In addition, clients 110, 112, and 114 are also connected to network 102. These clients 110, 112, and 114 may be, for example, personal computers, network computers, or the like. In the depicted example, server 104 provides data, such as boot files, operating system images, and applications to the clients 110, 112, and 114. Clients 110, 112, and 114 are clients to server 104 in the depicted example. Distributed data processing system 100 may include additional servers, clients, and other devices not shown.

In the depicted example, distributed data processing system 100 is the Internet with network 102 representing a worldwide collection of networks and gateways that use the Transmission Control Protocol/Internet Protocol (TCP/IP) suite of protocols to communicate with one another. At the heart of the Internet is a backbone of high-speed data communication lines between major nodes or host computers, consisting of thousands of commercial, governmental, educational and other computer systems that route data and messages. Of course, the distributed data processing system 100 may also be implemented to include a number of different types of networks, such as for example, an intranet, a local area network (LAN), a wide area network (WAN), or the like. As stated above, FIG. 1 is intended as an example, not as an architectural limitation for different embodiments of the present invention, and therefore, the particular elements shown in FIG. 1 should not be considered limiting with regard to the environments in which the illustrative embodiments of the present invention may be implemented.

As shown in FIG. 1, one or more of the computing devices, e.g., server 104, may be specifically configured to implement mechanisms for scalable and traceable healthcare analytics management. The configuring of the computing device may comprise the providing of application specific hardware, firmware, or the like to facilitate the performance of the operations and generation of the outputs described herein with regard to the illustrative embodiments. The configuring of the computing device may also, or alternatively, comprise the providing of software applications stored in one or more storage devices and loaded into memory of a computing device, such as server 104, for causing one or more hardware processors of the computing device to execute the software applications that configure the processors to perform the operations and generate the outputs described herein with regard to the illustrative embodiments. Moreover, any combination of application specific hardware, firmware, software applications executed on hardware, or the like, may be used without departing from the spirit and scope of the illustrative embodiments.

It should be appreciated that once the computing device is configured in one of these ways, the computing device becomes a specialized computing device specifically configured to implement the mechanisms of the illustrative embodiments and is not a general purpose computing device. Moreover, as described hereafter, the implementation of the mechanisms of the illustrative embodiments improves the functionality of the computing device and provides a useful and concrete result that facilitates scalable and traceable healthcare analytics management.

These computing devices, or data processing systems, may comprise various hardware elements which are specifically configured, either through hardware configuration, software configuration, or a combination of hardware and software configuration, to implement one or more of the systems/subsystems described herein. FIG. 2 is a block diagram of just one example data processing system in which aspects of the illustrative embodiments may be implemented. Data processing system 200 is an example of a computer, such as server 104 in FIG. 1, in which computer usable code or instructions implementing the processes and aspects of the illustrative embodiments of the present invention may be located and/or executed so as to achieve the operation, output, and external affects of the illustrative embodiments as described herein.

In the depicted example, data processing system 200 employs a hub architecture including north bridge and memory controller hub (NB/MCH) 202 and south bridge and input/output (I/O) controller hub (SB/ICH) 204. Processing unit 206, main memory 208, and graphics processor 210 are connected to NB/MCH 202. Graphics processor 210 may be connected to NB/MCH 202 through an accelerated graphics port (AGP).

In the depicted example, local area network (LAN) adapter 212 connects to SB/ICH 204. Audio adapter 216, keyboard and mouse adapter 220, modem 222, read only memory (ROM) 224, hard disk drive (HDD) 226, CD-ROM drive 230, universal serial bus (USB) ports and other communication ports 232, and PCI/PCIe devices 234 connect to SB/ICH 204 through bus 238 and bus 240. PCI/PCIe devices may include, for example, Ethernet adapters, add-in cards, and PC cards for notebook computers. PCI uses a card bus controller, while PCIe does not. ROM 224 may be, for example, a flash basic input/output system (BIOS).

HDD 226 and CD-ROM drive 230 connect to SB/ICH 204 through bus 240. HDD 226 and CD-ROM drive 230 may use, for example, an integrated drive electronics (IDE) or serial advanced technology attachment (SATA) interface. Super I/O (SIO) device 236 may be connected to SB/ICH 204.

An operating system runs on processing unit 206. The operating system coordinates and provides control of various components within the data processing system 200 in FIG. 2. As a client, the operating system may be a commercially available operating system such as Microsoft® Windows 7®. An object-oriented programming system, such as the Java™ programming system, may run in conjunction with the operating system and provides calls to the operating system from Java™ programs or applications executing on data processing system 200.

As a server, data processing system 200 may be, for example, an IBM eServer™ System P® computer system, Power™ processor based computer system, or the like, running the Advanced Interactive Executive (AIX®) operating system or the LINUX® operating system. Data processing system 200 may be a symmetric multiprocessor (SMP) system including a plurality of processors in processing unit 206. Alternatively, a single processor system may be employed.

Instructions for the operating system, the object-oriented programming system, and applications or programs are located on storage devices, such as HDD 226, and may be loaded into main memory 208 for execution by processing unit 206. The processes for illustrative embodiments of the present invention may be performed by processing unit 206 using computer usable program code, which may be located in a memory such as, for example, main memory 208, ROM 224, or in one or more peripheral devices 226 and 230, for example.

A bus system, such as bus 238 or bus 240 as shown in FIG. 2, may be comprised of one or more buses. Of course, the bus system may be implemented using any type of communication fabric or architecture that provides for a transfer of data between different components or devices attached to the fabric or architecture. A communication unit, such as modem 222 or network adapter 212 of FIG. 2, may include one or more devices used to transmit and receive data. A memory may be, for example, main memory 208, ROM 224, or a cache such as found in NB/MCH 202 in FIG. 2.

As mentioned above, in some illustrative embodiments the mechanisms of the illustrative embodiments may be implemented as application specific hardware, firmware, or the like, application software stored in a storage device, such as HDD 226 and loaded into memory, such as main memory 208, for executed by one or more hardware processors, such as processing unit 206, or the like. As such, the computing device shown in FIG. 2 becomes specifically configured to implement the mechanisms of the illustrative embodiments and specifically configured to perform the operations and generate the outputs described hereafter with regard to the mechanisms for scalable and traceable healthcare analytics management.

Those of ordinary skill in the art will appreciate that the hardware in FIGS. 1 and 2 may vary depending on the implementation. Other internal hardware or peripheral devices, such as flash memory, equivalent non-volatile memory, or optical disk drives and the like, may be used in addition to or in place of the hardware depicted in FIGS. 1 and 2. Also, the processes of the illustrative embodiments may be applied to a multiprocessor data processing system, other than the SMP system mentioned previously, without departing from the spirit and scope of the present invention.

Moreover, the data processing system 200 may take the form of any of a number of different data processing systems including client computing devices, server computing devices, a tablet computer, laptop computer, telephone or other communication device, a personal digital assistant (PDA), or the like. In some illustrative examples, data processing system 200 may be a portable computing device that is configured with flash memory to provide non-volatile memory for storing operating system files and/or user-generated data, for example. Essentially, data processing system 200 may be any known or later developed data processing system without architectural limitation.

In one use case scenario in which aspects of the illustrative embodiments may be implemented, the Centers for Medicare and Medicaid Services (CMS) established a hospital readmission reduction program under value-based care, which triggers a hospital to invest efforts to improve readmission measures by patient risk stratification, better resource allocation, and care management. IBM Watson Health™ developed a predictive model to identify patients with high risk of readmission within a certain amount of time after discharge from the indexed hospitalization. A given customer may be interested in this predictive model and would like to evaluate the model on its patients. The customer may like to further customize and deploy the model into its practice and address the needs. In order to serve the requests of the customer, the model provider must quickly enable the evaluation of models on different data sets, manage the request from different customers and support the customization as well as periodic requests for updates, and deploy the model in different settings. Furthermore, the system will enable the mechanism to improve model performance over time by continuous learning.

In another use case, more than 29 million Americans have diabetes, which requires appropriate management to control blood sugar level in a certain range to reduce serious health complications. IBM Watson Health™ developed a predictive model to proactively detect the hypoglycemia events in Type 1 diabetes patients with three hour lead time, which allows timely intervention to avoid hypoglycemia. A given customer manages tens of thousands of Type 1 diabetes patients and is interested in personalizing this general model to different patients and in dynamically adapting and improving the model based on the patients' daily behaviors and activities. In order to serve the requests of the customer, the model provider must quickly enable the evaluation of models on different patients, manage and support the personalization, and deploy the model and manage different versions of the model based on incremental learning.

Figure 3:
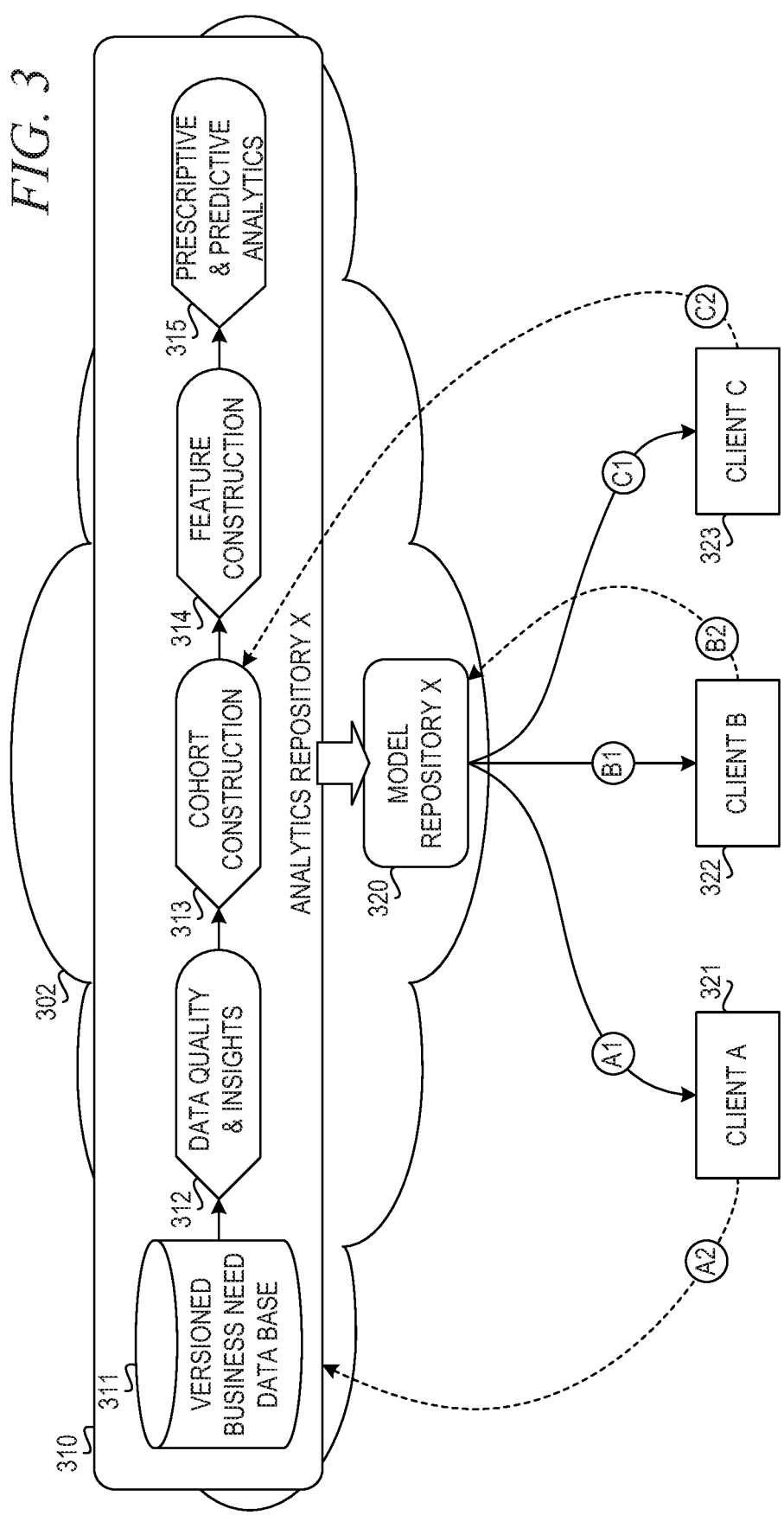
FIG. 3 depicts scalable and traceable healthcare analytics management in accordance with an illustrative embodiment.

FIG. 3 depicts scalable and traceable healthcare; analytics management in accordance with an illustrative embodiment. Analytics repository 310 is a versioned analytics repository with libraries of functions in each step of analytics workflow. In the depicted example, analytics repository 310 comprises versioned business need data base 311, data quality and insights component 312, cohort construction component 313, feature extraction component 314, and prescriptive and predictive analytics component 315 for version or instance X. Each version in analytics repository includes assets and libraries customized for each customer. Data quality and insights component 312 analyzes the business need data in data base 311 and generates insights from the data. Cohort construction component 313 identifies groups of patients based on attributes in the patient data for the study need. Feature construction component 314 identifies features that represent each population identified by cohort construction component 313. Prescriptive and predictive analytics component 315 predicts an outcome for a given patient and suggests actions to benefit from the predictions.

Model repository 320 is a versioned model repository linked to analytics repositories 310. Model repository 320 has not only the linkage to analytics repositories 310 but also all the metadata mentioned above to manage. In the depicted example, model repository 320 comprises a model for version or instance X. A model in model repository 320 is an abstracted mathematical equation derived retrospectively to predict something, such as a future event.

In accordance with an illustrative embodiment, analytics repository 310 and model repository 320 are embodied in a cloud computing environment 302. In step A1, a model deployment module (described in further detail below with reference to FIGS. 4 and 7) customizes and deploys a version or instance of an analytics model for client A 321. In step A2 of the depicted example, a model monitoring module (described in further detail below with reference to FIGS. 4 and 8) monitors the client A model and a model feedback module (described in further detail below with reference to FIGS. 4 and 9) detects a severe improvement need and performs feedback retraining to start of the analytics pipeline.

In step B1 of the depicted example, the model deployment module customizes and deploys a version or instance of an analytics model for client B 322. In step B2, the model monitoring module monitors the client B model and the model feedback module detects a minor improvement need and suggests parameter retuning in model repository 320.

In step C1 of the depicted example, the model deployment module customizes and deploys a version or instance of an analytics model for client C 323. In step C2, the model monitoring module monitors the client C model and the model feedback module detects a moderate improvement need and suggests cohort deviation in analytics repository 310.

In one embodiment, the healthcare analytics management system identifies analytic assets for a selected healthcare consumer based on a set of business needs for the selected healthcare consumer. The healthcare analytics management system then identifies a versioned healthcare model from a set of versions healthcare models based on the identified analytic assets, wherein the versioned model identifies data input requirements, key model parameters, runtime environment requirements, and performance measures and records corresponding to the identified analytic assets. The healthcare analytics management system evaluates the identified versioned healthcare model to ensure the versioned model meets the set of business needs for the selected healthcare consumer. Responsive to the identified versioned healthcare model meeting the set of business needs for the selected healthcare consumer, the healthcare analytics management system deploys the identified version healthcare model on a set of computing devices of the selected healthcare consumer.

Figure 4:
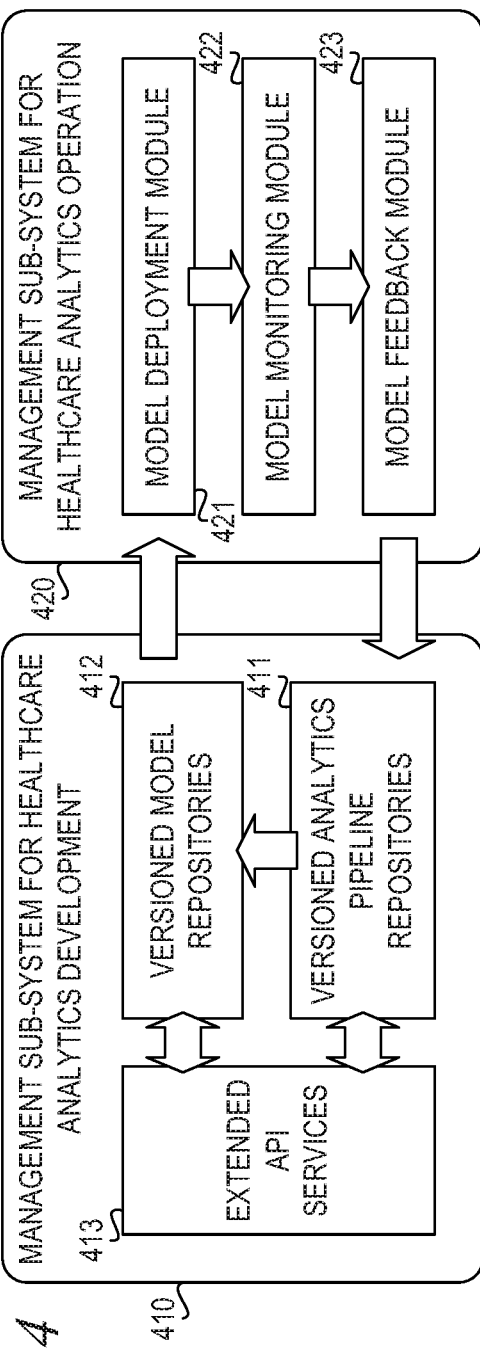
FIG. 4 is a block diagram depicting a system enabling cloud-based traceable and scalable healthcare analytics management in accordance with an illustrative embodiment.

FIG. 4 is a block diagram depicting a system enabling cloud-based traceable and scalable healthcare analytics management in accordance with an illustrative embodiment. The system orchestrates the end-to-end analytics lifecycle from development, operation, and feedback. The system includes two main sub-systems: a management sub-system for healthcare analytics development 410 and a management sub-system for healthcare analytics operation 420.

Management sub-system for healthcare analytics development 410 comprises versioned analytics pipeline repositories 411 with libraries of functions in each step of analytics workflow and versioned model repositories 412 linked to analytics repositories. Management sub-system for healthcare analytics development 410 also comprises extended application programming interface (API) services 413 for analytics functions as well as models developed. Extended API services 413 allow easy reuse and testing of versioned analytics pipelines 411 developed in different use cases, including data quality and insights, cohort construction, feature construction, descriptive and predictive analytics, etc. Extended API services 413 also allow a developer to easily run and evaluate versioned models 412 that were developed.

Versioned analytics pipeline repositories 411 capture the following:
1. analytics assets;
2. analytics workflow pipeline or dependency of assets;
3. any metadata or configuration data to support the workflow; and
4. key analytics key performance indicators (KPIs) or output results along the workflow.

Versioned model repositories 412 capture the following:
1. the trained model;
2. metadata that captures input data requirements;
3. metadata that captures runtime environment requirements;
4. metadata that captures the model parameters; and
5. metadata that captures the baseline model performance KPIs.

Management sub-system for healthcare analytics operation 420 comprises model deployment module 421, model monitoring module 422, and model feedback module 423. Model deployment module 421 plugs the right version of a model into the right runtime environment and actively manages the associated metadata. Model monitoring module 422 periodically reports the performance of deployed models and detects and notifies of performance deviations. Model feedback module 423 analyzes the potential root causes of performance deviations, reasons about improvement needs, and feeds improvement requirement needs back to management sub-system for healthcare analytics development 410.

In one embodiment, deployment module 421 includes functionality for model publication, model evaluation and, if needed, further adaption and customization before deployment. Deployment module 421 may publish the model for other customers to consider. Given that the illustrative embodiment has traceable analytics pipeline repositories and model repositories, the illustrative embodiment has the capability to transfer learning across clients, sharing feature insights across customers, sharing model knowledge across customers, etc. The model calibration/customization can happen in two different scenarios:
1. The model is particularly developed for one client; when in the deployment process, the production data is different from development data, and after model evaluation, adaption or customization is necessary.
2. The model is developed for one customer. Another customer sees the value of the model. In order to apply this model to the new customer, the model evaluation, adaption or customization is necessary.

Furthermore, deployment module 421 has not only the capability to deploy a single model but also the capability to deploy the aggregation of multiple models. For example, deployment module 421 may deploy an aggregation of multiple models including model composition, voting models, chaining models, etc.

Figure 5:
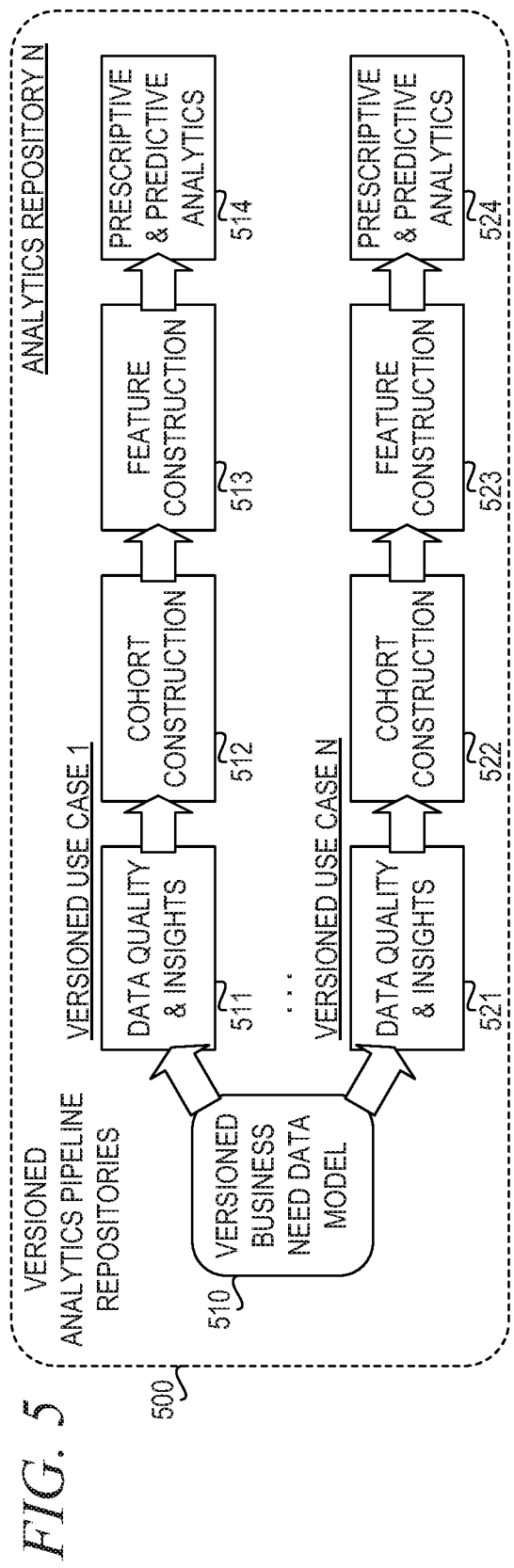
FIG. 5 is a block diagram depicting versioned analytics pipeline repositories in accordance with an illustrative embodiment.

FIG. 5 is a block diagram depicting versioned analytics pipeline repositories in accordance with an illustrative embodiment. FIG. 5 depicts versioned analytics pipeline repositories 500 for an analytics repository N, comprising versioned business need data model 510 and pipelines for a plurality of versioned use cases 1 to N, As shown, versioned use case 1 includes data quality and insights component 511, cohort construction component 512, feature construction component 513, and prescriptive and predictive analytics component 514, designed for the specific use case 1. Versioned use case N includes data quality and insights component 521, cohort construction component 522, feature construction component 523, and prescriptive and predictive analytics component 524, designed for the specific use case N, The analytics asset repositories are linked with versioned business need data model 510 developed by proprietary standards and organized by versioned use cases with componentized but end-to-end analytics workflow steps.

Figure 6:
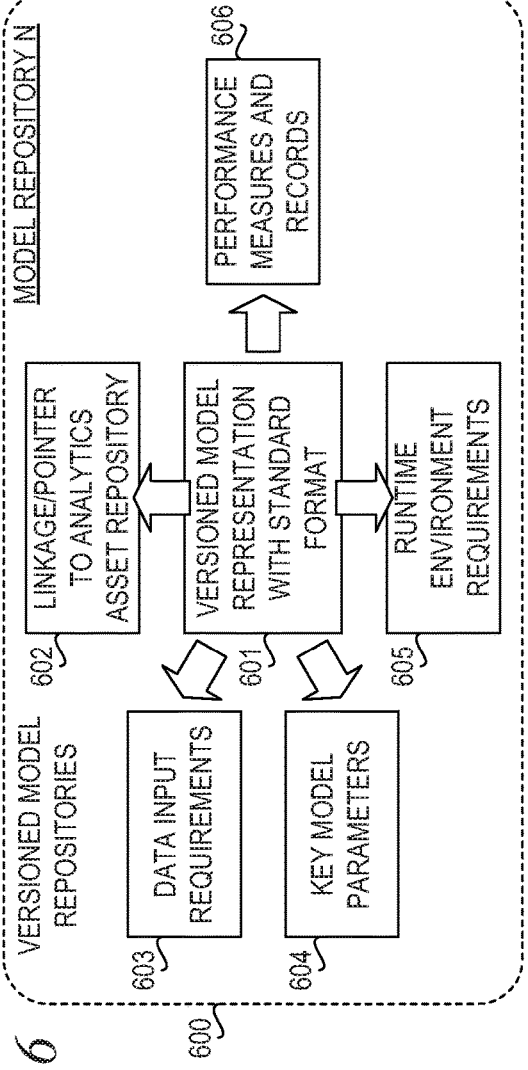
FIG. 6 is a block diagram depicting versioned model repositories in accordance with an illustrative embodiment.

FIG. 6 is a block diagram depicting versioned model repositories in accordance with an illustrative embodiment. In the depicted example, versioned model repositories 600 comprises model repository N for a given instance or version, which includes versioned model representation with standard format 601. The key component of a model repository is the versioned model representation 601 linked with the corresponding analytics asset repository 602 where the model was developed. The model repository also associates with data input requirements 603 and runtime environment requirements 605, which facilitate model deployment. Performance measures and records 606 establish the baseline for deployment performance, which allows further feedback benchmarks. Key model parameters 604 also serve a role in model calibration/customization and the feedback mechanism.

Figure 7:
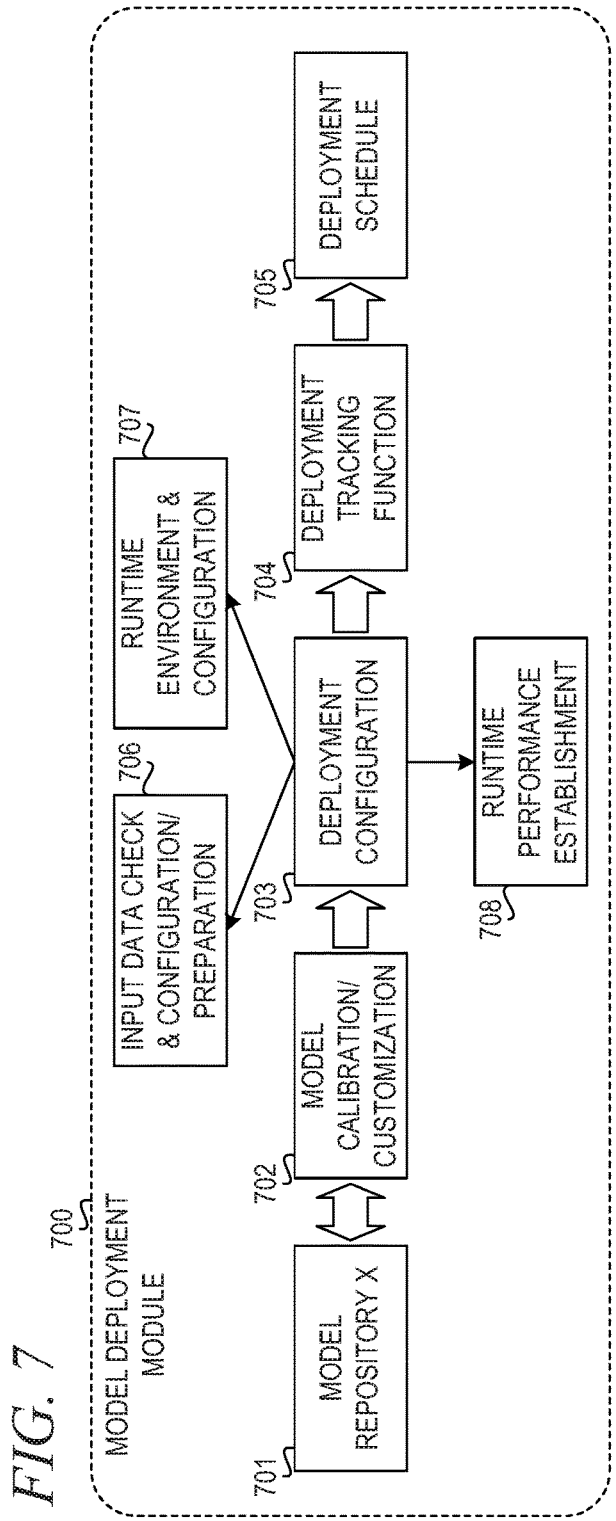
FIG. 7 is a block diagram depicting a model deployment module in accordance with an illustrative embodiment.

FIG. 7 is a block diagram depicting a model deployment module in accordance with art illustrative embodiment. Model deployment, module 700 deploys the models developed into the production environment and provides the analytic insights into business workflow. Model deployment module 700 closely links with version model repository 701. Model calibration/customization component 702 leverages the metadata in model repository 701 to execute deployment configuration 703. Model calibration/customization component 702 may modify data inputs, features used to define populations, or key model parameters. Model calibration/customization component 702 may revert to a previous version of the model.

Model deployment module 700 comprises input data check and configuration/preparation component 706 and runtime environment check and configuration 707, which perform checks, configurations, and preparations based on the deployment configuration. Input data check and configuration/preparation component 706 performs a check on the input data and configures and prepares the analytics model for deployment based on the input data. Model deployment module 700 also has the capability to specify the dependency of deployed analytics (deployment workflow graph). Runtime environment check and configuration component 707 performs a check on the runtime environment and configures the analytics model based on the runtime environment for deployment. Runtime performance establishment component 708 establishes the runtime performance against which the analytics model will be compared, as well as the key parameters of performance that will be included in feedback.

Model deployment module 700 also comprises deployment, tracking function 704 to manage the variety of different deployments in different sites as well as scheduling needs. Model deployment module 700 generates and executes deployment schedule 705 by which the various analytics modules are deployed to their respective runtime environments.

Figure 8:
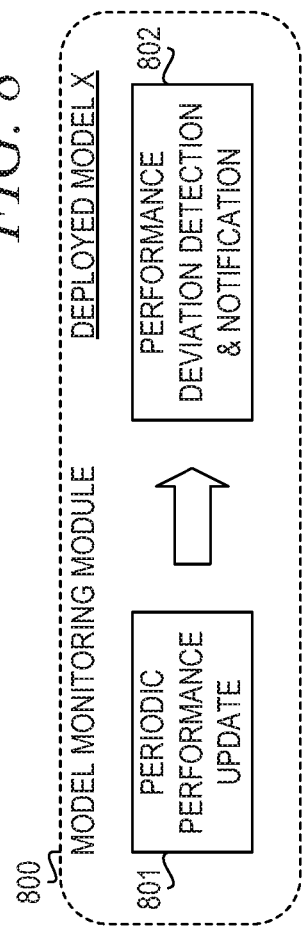
FIG. 8 is a block diagram depicting a model monitoring module in accordance with an illustrative embodiment.

FIG. 8 is a block diagram depicting a model monitoring module in accordance with an illustrative embodiment. In the depicted example, model monitoring module 700 comprises periodic performance update component 801, which periodically reports the performance of deployed model X. The frequency of model performance update component 801 depends on the nature of analytics as well as the availability of target data to provide performance evaluation.

Model monitoring module 800 also comprises performance deviation detection and notification component 802. When the model performance drops out of the normal range, performance deviation detection and notification component 802 detects the deviation of performance and generates an alarm or notification and sends the notification out for report.

Figure 9:
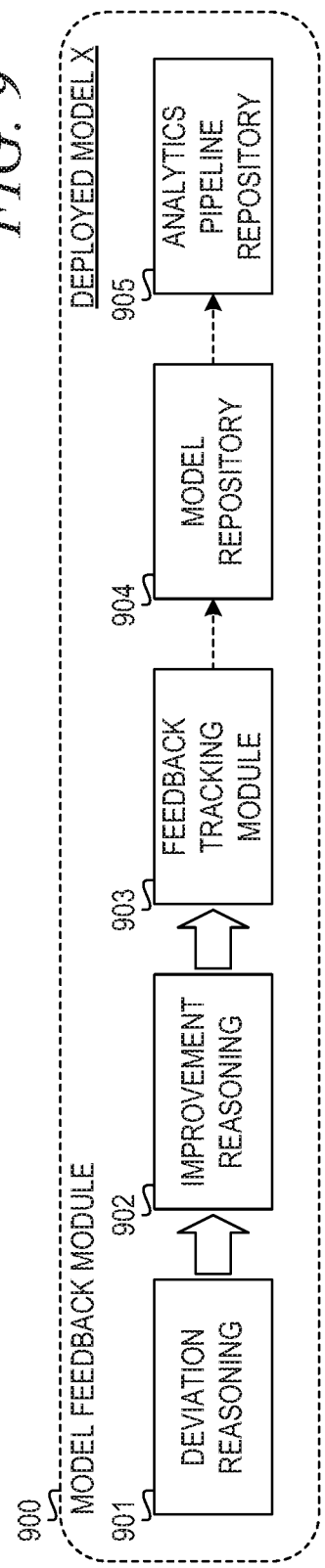
FIG. 9 is a block diagram depicting a model feedback module in accordance with an illustrative embodiment.

FIG. 9 is a block diagram depicting a model feedback module in accordance with an illustrative embodiment. The performance deviation notification generated by the model monitoring module triggers a reasoning process to investigate what are the underlying reasons for performance deviation, e.g., necessary features missing, distribution deviation of input features for predictive modeling, new data feed detection, automated hypotheses checking, etc. Deviation reasoning component 901 performs reasoning processing to determine the cause of the performance deviation.

Deviation reasoning component 901 may itself use analytics to determine the root cause of the performance deviation. For example, deviation reasoning component 901 may discover correlations between data inputs, features used to define populations, etc. and instances of performance degradation. Alternatively, or in addition, deviation reasoning component 901 may use machine learning by gathering past performance deviations and known causes as training data and training machine learning model based on the training data.

Deviation reasoning component 901 provides the identified root cause of the performance deviation to improvement reasoning function 902 to determine the need and level of retraining. Improvement reasoning function 902 analyzes the performance deviation data and the identified root cause to determine what portion(s) of the analytics pipeline in the analytics repository and/or model in the model repository need to be improved, intensity of retraining, and to what extent the improvement is needed. For example, improvement reasoning function 902 may identify improvement needs including: 1) minor update of model parameters; 2) moderate update of model structure and parameters; 3) intensive update of model, including adding or deleting input parameters, etc., which need to feed back to the analytics pipeline repository. Improvement reasoning function 902 may use analytics or machine learning. For instance, improvement reasoning function 902 may identify other clients that had the same issue and how the clients solved the issue. Improvement reasoning function 902 may identify the correlation using analytics and use the detected correlations as training instances.

Feedback tracking module 903 records all the necessary information for improvement retraining, e.g., the root cause of deviation, the need and intensity of retraining, the associated deployed model, model repository, pipeline repository, time stamp of event detection, etc. This recorded information may be used as training data for deviation reasoning and improvement need reasoning in future iterations using machine learning. Model feedback module 900 then feeds the improvement retraining information back to model repository 904 and analytics pipeline repository 905.

Figure 10:
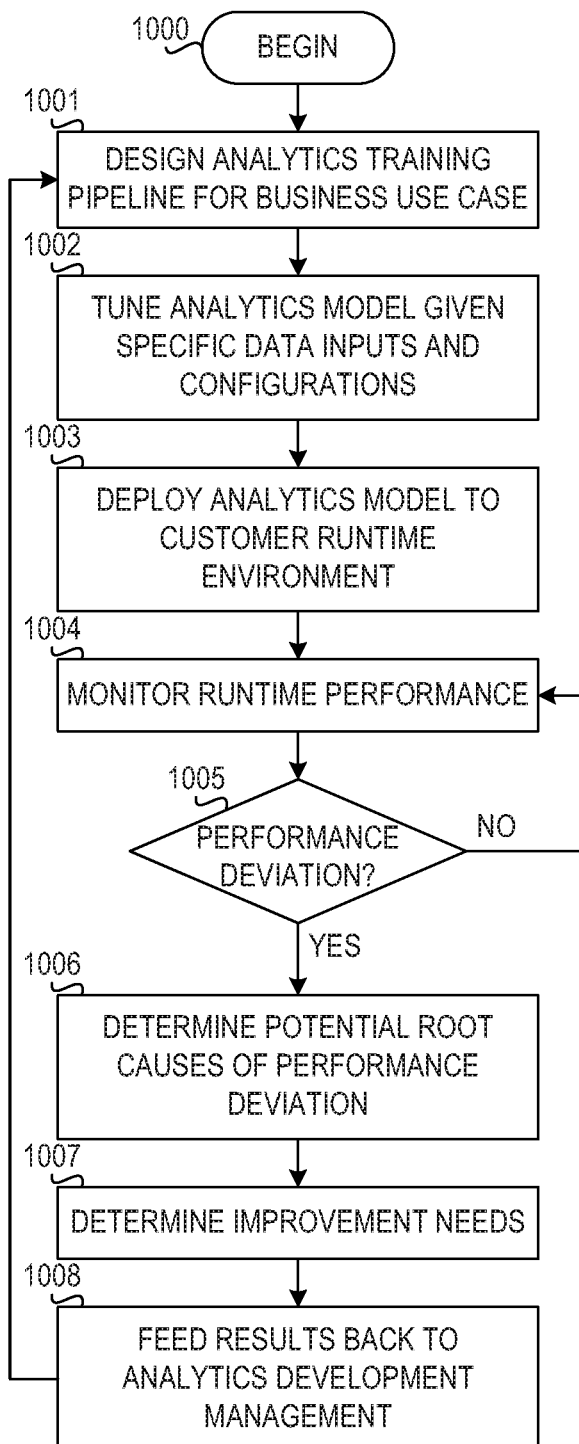
FIG. 10 is a flowchart illustrating operation of a mechanism for scalable and traceable healthcare analytics management in accordance with an illustrative embodiment.

FIG. 10 is a flowchart illustrating operation of a mechanism for scalable and traceable healthcare analytics management in accordance with an illustrative embodiment. Operation begins (block 1000), and a developer or data scientist designs an analytics training pipeline for a business use case (block 1001). The developer or data scientist tunes the analytics model given specific data inputs and configurations (block 1002). The analytics pipeline may be stored in a versioned analytics pipeline repository, and the analytics model may be stored in a versioned model repository.

A model deployment module deploys the analytics model to the customer runtime environment (block 1003). A model monitoring module then monitors the runtime performance (block 1004) and determines whether a performance deviation is detected (block 1005). If the model monitoring module does not detect a performance deviation, then operation returns to block 1004 to further monitor performance.

If the model monitoring module detects a performance deviation in block 1005, then a deviation reasoning component analyzes the model and the detected deviation to determine potential root causes of the performance deviation (block 1006). An improvement reasoning component determines improvement needs to adjust to the performance deviation (block 1007). Then, the mechanism feeds the results back to the analytics development management (block 1008). Thereafter, operation returns to adjust the analytics pipeline in the analytics pipeline repository in block 1001 and tune the analytics model in the analytics model repository in block 1002.

Thus, the illustrative embodiments facilitate analytics governance that reduces errors and improves efficiency in large-scale analytics assets operations. The illustrative embodiments provide a standardized approach to storing and versioning analytics pipelines and models. Assets are traceable at every step of the lifecycle. The illustrative embodiments enhance collaboration and reusability of assets through standard workflow, function libraries, and API services. The illustrative embodiments improve speed to analytics customization and deployment. The configurable analytics pipeline allows "tuning" of analytics assets to specific patient population characteristics or data. Assets are searchable, reusable, and extendable. The illustrative embodiments improve the accuracy and relevance of data-driven evidence with a closed loop continuous and adaptive learning system.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Java, Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

As noted above, it should be appreciated that the illustrative embodiments may take the form of an entirely hardware embodiment, an entirely software embodiment or an embodiment containing both hardware and software elements. In one example embodiment, the mechanisms of the illustrative embodiments are implemented in software or program code, which includes but is not limited to firmware, resident software, microcode, etc.

A data processing system suitable for storing and/or executing program code will include at least one processor coupled directly or indirectly to memory elements through a communication bus, such as a system bus, for example. The memory elements can include local memory employed during actual execution of the program code, bulk storage, and cache memories which provide temporary storage of at least some program code in order to reduce the number of times code must be retrieved from bulk storage during execution. The memory may be of various types including, but not limited to, ROM, PROM, EPROM, EEPROM, DRAM, SRAM, Flash memory, solid state memory, and the like.

Input/output or I/O devices (including but not limited to keyboards, displays, pointing devices, etc.) can be coupled to the system either directly or through intervening wired or wireless I/O interfaces and/or controllers, or the like. I/O devices may take many different forms other than conventional keyboards, displays, pointing devices, and the like, such as for example communication devices coupled through wired or wireless connections including, but not limited to, smart phones, tablet computers, touch screen devices, voice recognition devices, and the like. Any known or later developed I/O device is intended to be within the scope of the illustrative embodiments.

Network adapters may also be coupled to the system to enable the data processing system to become coupled to other data processing systems or remote printers or storage devices through intervening private or public networks. Modems, cable modems and Ethernet cards are just a few of the currently available types of network adapters for wired communications, Wireless communication based network adapters may also be utilized including, but not limited to, 802.11 a/b/g/n wireless communication adapters, Bluetooth wireless adapters, and the like. Any known or later developed network adapters are intended to be within the spirit and scope of the present invention.

The description of the present invention has been presented for purposes of illustration and description, and is not intended to be exhaustive or limited to the invention in the form disclosed. Many modifications and variations will be apparent to those of ordinary skill in the art without departing from the scope and spirit, of the described embodiments. The embodiment was chosen and described in order to best explain the principles of the invention, the practical application, and to enable others of ordinary skill in the art to understand the invention for various embodiments with various modifications as are suited to the particular use contemplated. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A method, in a data processing system comprising at least one processor and at least one memory, the at least one memory comprising instructions executed by the at least one processor to cause the at least one processor to implement a healthcare analytics management system, the method comprising:

developing, by a healthcare analytics development sub-system of the healthcare analytics management system, an analytics pipeline of a set of analytics assets based on a set of business needs for a healthcare analytics client and a healthcare analytics model based on the set of analytics assets and the set of business needs, wherein the healthcare analytics model links to the analytics pipeline;

deploying, by a model deployment module of a healthcare analytics operation sub-system of the healthcare analytics management system, the healthcare analytics model on a set of computing devices of the healthcare analytics client;

responsive to a model monitoring module of the healthcare analytics operation sub-system detecting a performance deviation of the deployed healthcare analytics model for performance deviation from the set of business needs for the healthcare analytics client, determining, by a model feedback module of the healthcare analytics operation sub-system, improvement needs for the healthcare analytics model using continuous learning based on a machine learning model;

feeding, by the model feedback module, the improvement needs back to the healthcare analytics development sub-system; and customizing, by the healthcare analytics development sub-system, the healthcare analytics model based on the improvement needs.

2. The method of claim 1, wherein the set of analytics assets comprises data quality and insights, cohort construction, feature construction, and prescriptive and predictive analytic.

3. The method of claim 1, wherein deploying the healthcare analytics model further comprises verifying one or more of input data checks, performing input data configuration, performing input data preparation, verifying one or more runtime environment checks, and performing runtime configuration.

4. The method of claim 1, further comprising storing the analytics pipeline in a versioned analytics pipeline repository, wherein the versioned analytics pipeline repository comprises reusable libraries and wherein the versioned analytics pipeline is annotated to indicate metadata.

5. The method of claim 4, wherein the versioned analytics pipeline repository captures at least one of:
  analytics assets;
  analytics workflow pipeline or dependency of assets;
  any meta/configuration data to support the workflow; or
  key performance indicators (KPIs) or output results along the workflow.

6. The method of claim 4, further comprising storing the healthcare analytics model in a versioned analytics model repository, wherein the versioned analytics model repository is annotated to indicate metadata.

7. The method of claim 6, wherein the model repository captures at least one of:
  metadata of input data requirements;
  metadata of runtime environment requirements;
  metadata of model parameters; or
  metadata of baseline model performance key performance indicators (KPIs).

8. The method of claim 6, further comprising exposing configuration parameters of the versioned analytics pipeline repository and the metadata of the versioned analytics model repository through an application programming interface.

9. The method claim 6, wherein customizing the healthcare analytics model based on the improvement needs comprises reverting to a previous version of the healthcare analytics model from the versioned analytics model repository.

10. The method of claim 1, wherein determining improvement needs for the healthcare analytics model comprises determining a root cause of the performance deviation and determining a model improvement based on the performance deviation and the determined root cause.

11. The method of claim 10, wherein determining improvement needs for the healthcare analytics model further comprises determining a need level associated with the model improvement.

12. The method of claim 1, wherein deploying the healthcare analytics model on the set of computing devices of the selected healthcare consumer comprises deploying an aggregation of a plurality of healthcare analytics models on the set of computing devices.

13. The method of claim 1, wherein customizing the healthcare analytics model based on the improvement needs comprises modifying data inputs, features used to define populations, or key model parameters.

14. The method of claim 1, further comprising performing, by a runtime environment check and configuration component of the healthcare analytics operation sub-system of the healthcare analytics management system, a check on a runtime environment for deployment on the set of computing devices healthcare analytics client.

15. The method of claim 14, further comprising configuring, by the runtime environment check and configuration component the analytics model based on the runtime environment for deployment.

16. The method of claim 1, further comprising establishing, by a runtime performance establishment component of the healthcare analytics operation sub-system of the healthcare analytics management system, a runtime performance against which the healthcare analytics model is to be compared and key parameters of performance that will be included in feedback.

* * * * *